United States Patent [19]

Ogami

[11] 4,177,802

[45] Dec. 11, 1979

[54] SELF RETAINING SKIN RETRACTOR

[76] Inventor: Noboru Ogami, 34 Gartley Pl., Honolulu, Hi. 96817

[21] Appl. No.: 862,811

[22] Filed: Dec. 21, 1977

[51] Int. Cl.² ............................................. A61B 17/04
[52] U.S. Cl. .................................................... 128/20
[58] Field of Search ........... 128/20, 76 B, 346, 334 R, 128/335, 345; 24/3 H, 3 J, 87 C, 87 TB, 152, 161; 223/61

[56]         References Cited
         U.S. PATENT DOCUMENTS

| 748,131 | 12/1903 | Winterbotham | 24/87 TB X |
| 928,424 | 7/1909 | Betts | 24/87 C X |
| 1,441,298 | 1/1923 | Pineiro | 128/334 |
| 2,234,715 | 3/1941 | Whitney | 128/345 X |
| 2,383,705 | 8/1945 | Bortagaray | 128/20 |

*Primary Examiner*—Clifford D. Crowder
*Assistant Examiner*—James R. Feyrer
*Attorney, Agent, or Firm*—Robert E. Geauque

[57] ABSTRACT

A device to facilitate accurate placing of sutures for closing a wound or incision which takes the form of an elongated wire member the ends of which are to be located at the ends of the wound or incision. The device is to be resilient forcing outwardly the ends of the device and thereby making the wound or incision taut. The side walls of the wound or incision are maintained in accurate apposition so as to facilitate the location of the sutures.

5 Claims, 6 Drawing Figures

SELF RETAINING SKIN RETRACTOR

BACKGROUND OF THE INVENTION

The field of this invention relates to a device which is designed to assist surgeons in accurately and neatly locating sutures in the closing of abdominal wounds or incisions.

In the performing of surgical operations on the extremity of the human being, normally the incisions are small and also the skin is of sufficient inherent tautness that the closing of the incision present little difficulty in connecting together the sides of the incision in order to avoid bulging of the tissues and other unsightly irregularities in making the closure. However, in dealing with the abdominal area, much difficulty is had.

In most types of abdominal wound closures, multiple sutures must be placed at a predetermined distance in from the edge of the wound and must be spaced at predetermined spaced intervals along the longitudinal length of the incision. Heretofore, surgeons have had to judge the closing of the incision and the locating of the sutures so as to avoid bulging of the tissues between sutures and other irregularities in the closure. At times, the resulting closure is far short of ideal.

Previously, there have been known devices which facilitate the location of the sutures for the closing of a wound or incision. However, the known previous devices have been difficult to use and therefore, during an intricate procedure such as a surgical operation, the devices are seldom used.

There is a definite need for a device which facilitates the location of sutures for the closing of an abdominal wound or incision with such device being of simple construction and can be quickly and easily located to facilitate location of the sutures and after the wound is closed, can be readily removed without causing injury to the patient, or damage to the closure.

SUMMARY OF THE INVENTION

A skin retractor device which takes the form of an elongated wire rod body which is capable of being slightly bowed thereby producing resilience. The ends of the body are bent into right angle sections with the resilience tending to force outwardly the right angled end sections. The outermost portion of each of the ends are to be located at the ends of the incision with the resilience of the retractor causing the incision to be stretched. The width of the incision is therefore narrowed and the side walls of the incision are located in accurate apposition in respect to each other. Therefore, neat suturing of the incision can then be accomplished.

DETAILED DESCRIPTION OF THE SHOWN EMBODIMENT

Figure 1:
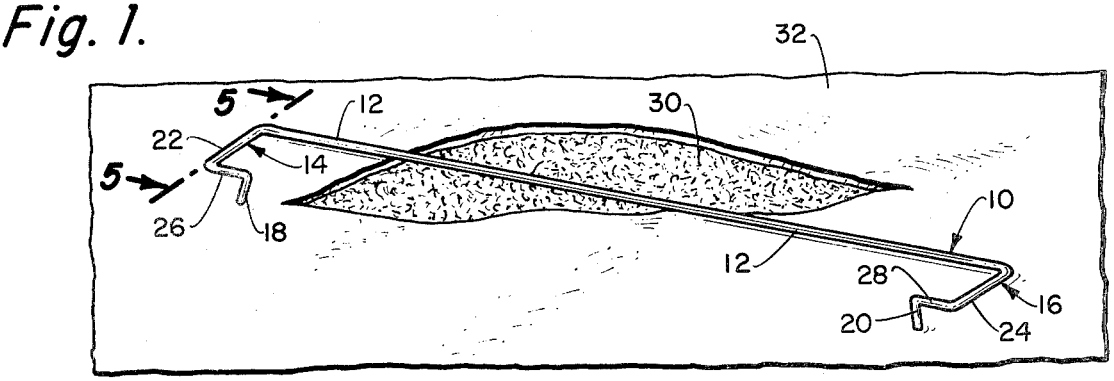
FIG. 1 is an isometric view of the skin retractor of this invention depicting such in relation to an open incision.

Referring particularly to the drawing, there is shown the skin retractor 10 of this invention which comprises a narrow and elongated body portion 12 which terminates into a first end 14 and the second end 16. The ends 14 and 16 are constructed to be substantially mirror images of each other with the exception of the outermost sections 18 and 20 of the ends 14 and 16, respectively, extend in the same lateral direction from the body portion 12.

The end 14 includes a first member 22 which is attached to the body portion 12 and is bent at approximately a right angle in respect thereto. A similar member 24 is included as part of end 16.

A second member 26 is integrally attached to member 22 and is located at a substantially right right angle thereto and is also located substantially parallel to the body 12. A similar member 28 is included within the end 16.

The section 18 is integrally attached to the member 26 and extends substantially at a right angle in respect thereto. Similarly, section 20 is integrally attached to the member 28 at a substantially right angle thereto.

The preferable construction material of the skin retractor 10 is a wire rod. This wire rod inherently provides a certain amount of bowing of the body 12. This bowing produces a resiliency, which, when in the bowed condition, exerts a force such that tending to move the ends 14 and 16 in the outward direction. This bowed arrangement is most desireable as will become apparent in the following description.

Figure 2:
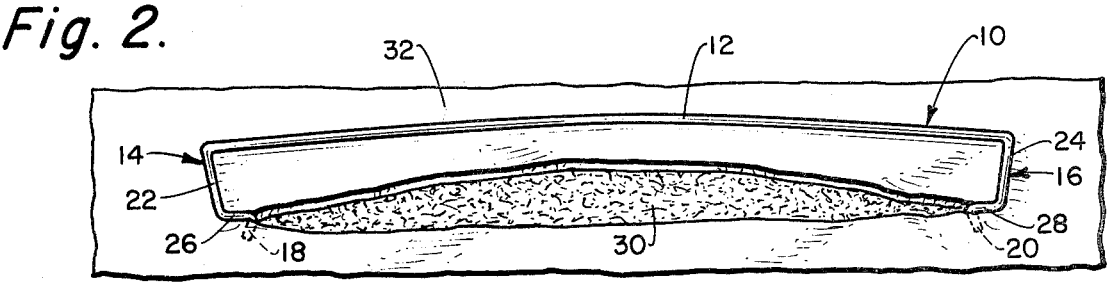
FIG. 2 is a view similar to FIG. 1 but showing the skin retractor in use with the suturing procedure having been initiated.
Figure 3:
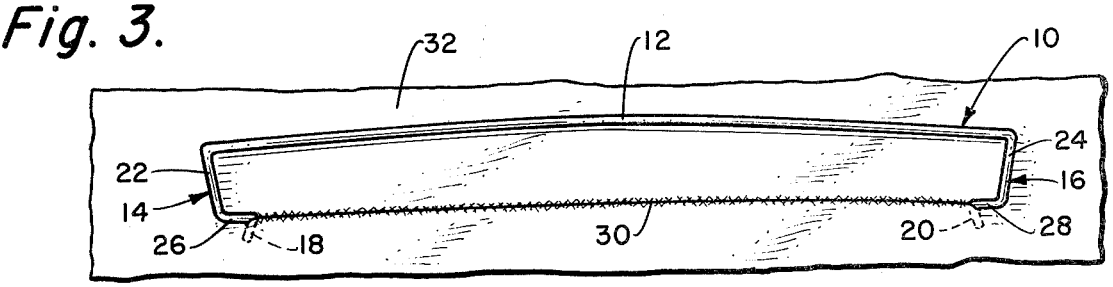
FIG. 3 is a view similar to FIG. 2 but showing the suturing procedure complete.
Figure 4:
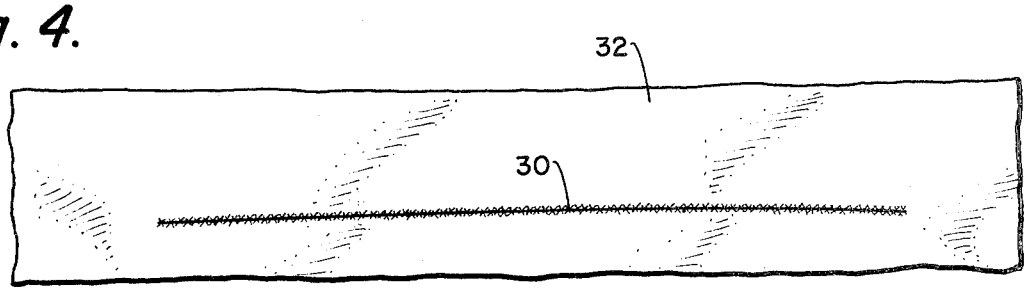
FIG. 4 is a view similar to FIG. 3 with the suturing procedure having been completed.
Figure 5:
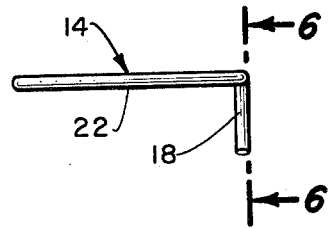
FIG. 5 is an end view of the skin retractor of this invention taken along line 5—5 of FIG. 1.
Figure 6:
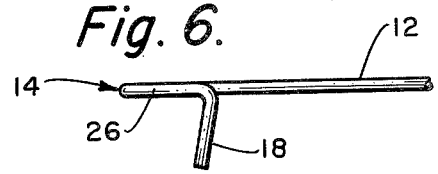
FIG. 6 is a bottom view of one end of the skin retractor of this invention taken along line 6—6 of FIG. 5.

When it is desired to close a surgical incision 30 (or wound) by a known suturing technique, a length of skin retractor is selected that is slightly longer than the length of the incision 30. The physician will have at his immediate disposal a selection of different lengths of skin retractor 10. The physician then physical bows the body 12 until the sections 18 and 20 can be placed under the skin 32 at opposite ends of the incision 30 as shown in FIGS. 2 and 3 of the drawing. The physician then releases the skin retractor 10 which permits the inherent resiliency of the skin retractor 10 to stretch taut the side walls of the skin 32 in the area of the incision 30. This tautness, to some extent, causes the incision 30 to somewhat close and it also brings the side walls of the incision in correct alignment with each other. The physician then proceeds to suture the incision closed by his own preference of suturing technique. As shown in the drawing, the continuous sub-cuticular technique is employed. The tautness of the side walls of the incision act as a counter-traction. The passing of the sewing needle through the sub-cuticular layer of skin results in simplification of suturing with the needle.

It is to be understood that the device of this invention could be employed with other conventional suturing techniques such as what is referred to the interrupted skin suturing technique and also the use of a plurality of closely spaced metallic clips to hold the edges of the wound together instead of a needle.

Once the incision 30 is closed, the device 10 is removed. As a result of using of the device 10, the closing of the wound is neat in appearance, no bulging of skin tissues or the producing of any recessed areas in the closing of the incision is present. As a result, the produced scar will be minimized. Also because the closure is so complete and accurate, infection is minimized.

Therefore, what is claimed is:

1. A skin retractor for use during suturing of an incision comprising:
    an elongated narrow body having a first end and a second end;
    a first connecting end attached to said first end, said first connecting end including a first member extending substantially at a right angle from said body a second member extending substantially at a right angle from said first member;
    a second connecting end attached to said second end, said second connecting end including a third member extending substantially at a right angle from said body and a fourth member extending substantially at a right angle from said third member;
    said first end and said second end to be located at opposite ends of the surgical incision causing slight stretching of the incision resulting in the incision side walls being stretched taut to maintain accurate apposition of the incision side walls to facilitate satisfactory closing of the incision and subsequently the most desirable incision scar in appearance;
    a fifth member connected to and extending substantially at a right angle from said second member, said fifth member being positioned substantially perpendicular to said body;
    a sixth member extending from and being connected to at substantially a right angle from said fourth member, said sixth member being positioned substantially parallel to said fifth member; and
    a seventh member connected to and extending angularly outwardly from said fifth member, an eighth member connected to and extending angularly outwardly from said sixth member, in respect to said body the said seventh and eighth members extend in substantially the same direction.

2. Skin retractor as defined in claim 1 wherein:
    said body being resilient so as to force outwardly both said first and said second ends with said skin retractor in use.

3. Skin retractor as defined in claim 2 wherein:
    said body comprising an elongated rod, said resiliency being provided by causing said rod to be bowed.

4. Skin retractor as defined in claim 3 wherein:
    said second member being parallel to said body, said fourth member being parallel to said body.

5. Skin retractor as defined in claim 4 wherein:
    said second member and said fourth member being located in a mirror image relationship in respect to each other.

* * * * *